(12) United States Patent
Rezaie et al.

(10) Patent No.: US 7,247,453 B1
(45) Date of Patent: Jul. 24, 2007

(54) CALCIUM BINDING RECOMBINANT ANTIBODY AGAINST PROTEIN C

(75) Inventors: Alireza Rezaie, Moore, OK (US); Charles T. Esmon, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 08/259,321

(22) Filed: Jun. 10, 1994

Related U.S. Application Data

(60) Continuation-in-part of application No. 07/982,832, filed on Nov. 30, 1992, now Pat. No. 5,336,610, which is a division of application No. 07/730,040, filed on Jul. 12, 1991, now Pat. No. 5,202,253, which is a continuation of application No. 07/292,447, filed on Dec. 30, 1988, now abandoned.

(51) Int. Cl.
*C12P 21/08* (2006.01)
*A61K 39/395* (2006.01)
*C07K 16/18* (2006.01)

(52) U.S. Cl. .................. 435/69.6; 435/70.1; 435/71.2; 424/133.1; 424/141.1; 530/387.1; 530/387.3; 530/388.1

(58) Field of Classification Search ............. 530/387.3, 530/388.25, 391.1, 391.3, 387.1, 388.1; 536/23.53; 435/240.2, 240.27, 70.21, 172.2, 320.1, 252.3, 435/326, 328, 69.1, 69.6, 70.1, 71.2; 424/133.1, 424/141.1

See application file for complete search history.

(56) References Cited

U.S. PATENT DOCUMENTS

| | | | |
|---|---|---|---|
| 4,506,009 | A | 3/1985 | Lenhoff et al. |
| 5,147,638 | A | 9/1992 | Esmon et al. |
| 5,202,253 | A | 4/1993 | Esmon et al. |
| 5,298,599 | A | 3/1994 | Rezaie et al. |
| 5,336,610 | A | 8/1994 | Esmon et al. |
| 5,530,101 | A * | 6/1996 | Queen |

FOREIGN PATENT DOCUMENTS

WO    9007861    *    7/1990

OTHER PUBLICATIONS

Morrison, Science 229:1201-7, 1985.*
D'Angelo et al. J. Clin. Invest. 77:416-425, 1986.*
Beckmann Robert J et al "The structure and evolution of a 461 amino acid human protein C precursor and its messenger RNA based upon the DNA sequence of cloned human liver cDNAs," *Nucleic Acids Res.* 13(14):5233-5246 (1985).
Colman, R.W., et al., Hemostatis and Thrombosis: Basic Principles and Clinical Practice 2nd Ed., p. 263 (J.B.Lippincott, Philadelphia, PA 1987).
Daugherty, et al., Nucl. Acids Res., 19:2471-2476 (1991).
Dreyfus, Marie, et al., "Treatment of Homozygous Protein C Deficiency and Neonatal Purpura Fulminans with a Purified Protein C Concentrate," *New England Journal of Medicine* 325(22):1565-1568 (1991).
Esmon, Charles T., "The Regulation of Natural Anticoagulant Pathways," *Science* 235:1348-1352 (1987).
Esmon, Charles T., "the Roles of Protein C and Thrombomodulin in the Regulation of Blood Coagulation," *J. of Biol. Chem.* 264(9):4743-4746 (1989).
Esmon, C. T., et al., at the Joint IABS/CSL Symposium on Standardization in Blood Fractionation including Coagulation Factors, Melbourne, Australia 1986 (reported in *Develop. Biol. Standard.*, 67:51-57 (S. Karger, Basel, 1987).
Esmon, C.T., et al., at the Joint IABS/CSL Symposium on Standardization in Blood Fractionation incluidng Coagulation Factors, Melbourne, Australia 1986 in *Develop. Biol. Standard*, 67:75-82 (S. Karger, Basel, 1987).
Frevssinet J.M., et al., "Inhibition of Human Protein C Activation by Vitamin K-dependent Proteins, Involvement of the γ-Carboxyglutamic Acid Domain in Distinct Interactions with the Human Thrombin-Thrombomodulin Complex and Phospholipids," *Thrombosis and Haemostasis* 58(1):230 (1987).
Goding, James W., "Purification, Fragmentation and Isotopic Labelling," Monoclonal Antibodies: Principles and Practices 110-113 (Academic Press, Inc.) (1983).
Hendl, Sylvia, et al., "Immunoaffinity purification of protein C with a calcium-dependent monoclonal antibody," *Rev. Iberoamer Thromb. Hemostasia* 4(1):25-28 (1991).
Hongo, Tasuku et al. *Cell* 18:559-566, (1979).
Ikeda, Kyoichi and Johan Stenflo, "A Radioimmunoassay for Protein C." *Thrombosis Research* 39:297-306 (1985).
Kisiel, in *J. Clin. Invest* 64, 761-769 (1979).
Kobilka, B.K., et al. "Chimeric $\alpha_2$-$\beta_2$-Adrenergic Receptors: Delineation of Domains Involved in Effector Coupling and Ligand Binding Specificity" *Science* 240:1310-1316 (1988).
Laurell, Martin, et al., "Characterization of monoclonal antibodies against human protein C specific for the calcium ion-induced comformation or for the activation peptide region," *FEBS Letts.* 191(1):75-81 (1985).
Matschiner, et al., *Current Advances in Vitamin K Research*, pp. 135-140, John W. Suttie, ed. (Elsevier Science Publishing Co., Inc. 1988).
Max, Edward, et al, *J. Biol. Chem.* 256:5116-5120 (1981).
Nakamura, Satoko and Yoichi Sakata, "Immunoaffinity purification of protein C by using conformation-specific monoclonal antibodies to protein C-calcium ion complex," *Biochimica et Biophysica Act* 925:85-93 (1987).

(Continued)

*Primary Examiner*—Karen A. Canella
(74) *Attorney, Agent, or Firm*—Fulbright & Jaworski

(57) ABSTRACT

A $Ca^{2+}$ dependent recombinant antibody that specifically binds to a specific twelve peptide sequence (E D Q V D P R L I D G K) in the activation region of the Protein C has been constructed. The antibody does not bind to Activated Protein C and can be used to inhibit activation of Protein C by thrombin-thrombomodulin, in purification of Protein C, and in treatment of tumors.

20 Claims, No Drawings

OTHER PUBLICATIONS

Ohlin, Ann-Kristin and Johan Stenflo, "Calcium-dependent Interaction between the Epidermal Growth Factor Precursor-like Region of Human Protein C and a Monoclonal Antibody," *J. Biol. Chem.* 262:13798-13804 (1988).

Ohlin, A. K., and J. Stenflo, "High Affinity Calcium to Domaines of Protein C That are Homologus to the Epidermal Growth Factor," *Thrombosis and Haemostatis* 58(1):230 (1987).

Riechmann.L., M. Clark, H Waldmann. G, Winter, "Reshaping human antibodies for therapy," *Nature*, 332:323-327 (1988).

Seligsohn, Uri, et al., "Homozygous Protein C Deficiency Manifested by Massive Venous Thrombosis in the Newborn," *New England J. of Medicine* 310(9):559-562 (1984).

Stearns, Deborah, et al., "The Interaction of a $Ca^{2+}$-dependent Monoclonal Antibody with the Protein C Activation Peptide Region," *J. Biol Chem.* 263(2):826-832 (1988).

Sugo, et al., Thromb. Hemost. Abstrs., Brussells, 229 (1987).

Summers, M.D. and G.E. Smith, "A manual of methods for baculovirus vectors and insect cell culture procedures". Texas Agricultural Experimental Station (1987).

Suzuki, Kobi, et al., "Monoclonal Antibodies to Human Protein C: Effects on the Biological Activity of Activated Protein C and the Thrombin-Catalyzed Activation of Protein C," *J. Biochem.* 97:127-138 (1985).

Taylor, F. B., et al., "Protein C Prevents the Coagulopathic and Lethal Effects of *Escherichia coli* Infusion in the Baboon," *J. Clin. Invest.* 79:918-925 (1987).

Verhoeven, M., C. Milstein, G. Winter, "Reshaping Human Antibodies: Grafting an Antilysozyme Activity," *Science*, 239:1534-1536 (1988).

Vukovich, Thomas, et al., "Replacement therapy for a homozygous protein C deficiency-state using a concentrate of human protein C and S," *British J. of Haematology* 70:435-440 (1988).

Wakabayashi, et al., *J. Biol. Chem.* 261, 11097-11105 (1986).

\* cited by examiner

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: Internal (xi) SEQUENCE DESCRIPTION: SEQ ID NO:1:

Glu Asp Gln Val Asp Pro Arg Leu Ile Asp Gly Lys
1               5                   10

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:2:

AAGCGGCCGC TGGATAGACA GATGGGGGTG TCGTTTTGCC                              40

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

AAGCGGCCGC CCCCCCCCCC CCCCCCCCCC                                         30

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:4:

AAGCGGCCGC GAAGATGGAT ACAGTTGGTG CAGCATCAGC                              40

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:5:

AGGTTACTCT GCTCGAGTCT GGCCCTGG                                              28

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:6:

AGGCCTACTA GTTTACTAAC AATCCCTGGG CACAAT                                     36

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

TGTCCAGAGG AGAGCTCATT CTCACCCAGT CTCCGGC                                    37

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:8:

TCCTTCTAGA TTACTAACAC TCTCCCCTGT TGAA                                       34

(2) INFORMATION FOR SEQ ID NO:9:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: HPC-4 Heavy Chain Variable Region (VH Gamma)

(ix) FEATURE:

(A) NAME/KEY: misc_feature
(B) LOCATION: 1..57
(D) OTHER INFORMATION: /note= "Signal peptide encoded by nucleotides 1 through 5

(ix) FEATURE:
(A) NAME/KEY: misc_feature
(B) LOCATION: 58..417
(D) OTHER INFORMATION: /note= "Mature peptide encoded by nucleotides 58 through (xi) SEQUENCE DESCRIPTION: SEQ ID NO:9:

```
ATGGGCAGGC TTTCTTCTTC ATTCTTGCTA CTGATTGCCC CTGCATATGT CCTGTCCCAG      60
GTTACTCTGA AAGAGTCTGG CCCTGGGATA TTGCAGCCCT CCCAGACCCT CACTCTGACT     120
TGTTCTCTCT CTGGGTTTTC ACTGAGGACT TCTGGTATGG GTGTAGGCTG GATTCGTCAG     180
CCTTCAGGGA AGGGTCTGGA GTGGCTGGCA CACATTTGGT GGGATGATGA CAAGCGCTAT     240
AACCCAGTCC TGAAGAGCCG ACTGATAATC TCCAAGGATA CCTCCAGGAA ACAGGTATTC     300
CTCAAGATCG CCAGTGTGGA CACTGCAGAT ACTGCCACAT ACTACTGTGT TCGAATGATG     360
GATGATTACG ACGCTATGGA CTACTGGGGT CAAGGAACCT CAGTCACCGT CTCCTCT       417
```

(2) INFORMATION FOR SEQ ID NO:10:

(i) SEQUENCE CHARACTERISTICS:
(A) LENGTH: 139 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: Internal (vi) ORIGINAL SOURCE:
(A) ORGANISM: HPC-4 Heavy Chain Variable Region (VH Gamma)

(ix) FEATURE:
(A) NAME/KEY: misc_feature
(B) LOCATION: 20..139
(D) OTHER INFORMATION: /note= "Gln at position 20 starts mature peptide."

(xi) SEQUENCE DESCRIPTION: SEQ ID NO:10:

```
Met Gly Arg Leu Ser Ser Ser Phe Leu Leu Leu Ile Ala Pro Ala Tyr
  1               5                  10                  15

Val Leu Ser Gln Val Thr Leu Lys Glu Ser Gly Pro Gly Ile Leu Gln
             20                  25                  30

Pro Ser Gln Thr Leu Thr Leu Thr Cys Ser Leu Ser Gly Phe Ser Leu
         35                  40                  45

Arg Thr Ser Gly Met Gly Val Gly Trp Ile Arg Gln Pro Ser Gly Lys
     50                  55                  60

Gly Leu Glu Trp Leu Ala His Ile Trp Trp Asp Asp Asp Lys Arg Tyr
 65                  70                  75                  80

Asn Pro Val Leu Lys Ser Arg Leu Ile Ile Ser Lys Asp Thr Ser Arg
                 85                  90                  95

Lys Gln Val Phe Leu Lys Ile Ala Ser Val Asp Thr Ala Asp Thr Ala
            100                 105                 110

Thr Tyr Tyr Cys Val Arg Met Met Asp Asp Tyr Asp Ala Met Asp Tyr
        115                 120                 125
```

```
Trp Gly Gln Gly Thr Ser Val Thr Val Ser Ser
    130                 135
```

(2) INFORMATION FOR SEQ ID NO:11:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: HPC-4 Light Chain Variable Region (VL Kappa)

(ix) FEATURE:
        (A) NAME/KEY: misc_feature
        (B) LOCATION: 1..66
        (D) OTHER INFORMATION: /note= "Signal peptide encoded by
            nucleotides 1 through 6

(ix) FEATURE:
        (A) NAME/KEY: misc_feature
        (B) LOCATION: 67..387
        (D) OTHER INFORMATION: /note= "Mature peptide encoded by
            nucleotides 67 through (xi) SEQUENCE DESCRIPTION: SEQ ID NO:11:

```
ATGGATTTTC AGGTGCAGAT TTTCAGCTTC CTGCTAATCA GTGCCTCAGT CATAATGTCC      60

AGAGGACAAA TTATTCTCAC CCAGTCTCCG GCAATCATGT CTGCATCTCT GGGGGAGGAG     120

ATCACCCTAA CCTGCAGTGC CACTTCGAGT GTAACTTACG TCCACTGGTA CCAGCAGAAG     180

TCAGGCACTT CTCCCAAACT CTTGATTTAT GGGACATCCA ACCTGGCTTC TGGAGTCCCT     240

TCTCGTTTCA GTGGCAGTGG GTCTGGGACC TTTTATTCTC TCACAGTCAG CAGTGTGGAG     300

GCTGAAGATG CTGCCGATTA TTACTGCCAT CAGTGGAATA GTTATCCGCA CACGTTCGGA     360

GGGGGGACCA AGCTGGAAAT AAAACGG                                        387
```

(2) INFORMATION FOR SEQ ID NO:12:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: HPC-4 Light Chain Variable Region (VL Kappa)

(ix) FEATURE:
        (A) NAME/KEY: misc_feature
        (B) LOCATION: 23..129
        (D) OTHER INFORMATION: /note= "Gln at position 23 starts
            mature peptide."

(xi) SEQUENCE DESCRIPTION: SEQ ID NO:12:

```
Met Asp Phe Gln Val Gln Ile Phe Ser Phe Leu Leu Ile Ser Ala Ser
1               5                   10                  15
```

-continued

```
Val Ile Met Ser Arg Gly Gln Ile Ile Leu Thr Gln Ser Pro Ala Ile
            20              25              30

Met Ser Ala Ser Leu Gly Glu Glu Ile Thr Leu Thr Cys Ser Ala Thr
        35              40              45

Ser Ser Val Thr Tyr Val His Trp Tyr Gln Gln Lys Ser Gly Thr Ser
    50              55              60

Pro Lys Leu Leu Ile Tyr Gly Thr Ser Asn Leu Ala Ser Gly Val Pro
65              70              75              80

Ser Arg Phe Ser Gly Ser Gly Ser Gly Thr Phe Tyr Ser Leu Thr Val
            85              90              95

Ser Ser Val Glu Ala Glu Asp Ala Ala Asp Tyr Tyr Cys His Gln Trp
            100             105             110

Asn Ser Tyr Pro His Thr Phe Gly Gly Gly Thr Lys Leu Glu Ile Lys
        115             120             125

Arg
```

CALCIUM BINDING RECOMBINANT ANTIBODY AGAINST PROTEIN C

This is a continuation-in-part of U.S. Ser. No. 07/982,832 filed Nov. 30, 1992 now U.S. Pat. No. 5,336,610, which is a divisional of U.S. Ser. No. 07/730,040 filed Jul. 12, 1991, issued as U.S. Pat. No. 5,202,253 Apr. 13, 1993, which is a continuation of U.S. Ser. No. 07/292,447 filed Dec. 30, 1988 now abandoned.

BACKGROUND OF THE INVENTION

This invention is generally in the area of antibodies to plasma proteins, specifically Protein C, and methods for use thereof.

Protein C is a vitamin K-dependent plasma protein zymogen to a serine protease. Upon activation it becomes a potent anticoagulant. Activated protein C acts through the specific proteolysis of the procoagulant cofactors, factor VIIIa and factor Va. This activity requires the presence of another vitamin K-dependent protein, protein S, calcium and a phospholipid (presumably cellular) surface. As described in *Hemostasis and Thrombosis: Basic Principles and Clinical Practice* 2nd Ed., Colman, R. W., et al., p. 263 (J.B.Lippincott, Philadelphia, Pa. 1987), protein C circulates in a two-chain form, with the larger, heavy chain bound to the smaller light chain through a single disulfide link. A small proportion of the protein also circulates in a single chain form, where a Lys-Arg dipeptide in the molecule connects the light chain directly to the heavy chain.

Protein C is activated to activated protein C (APC). Thrombin is capable of activating protein C by the specific cleavage of the $Arg^{12}$-$Leu^{13}$ bond in the heavy chain. In vivo, in the presence of physiological concentrations of calcium, the rate of this activation is enhanced dramatically when thrombin is bound to the endothelial cell cofactor, thrombomodulin. Matschiner, et al., *Current Advances in Vitamin K Research*, pp. 135–140, John W. Suttie, ed. (Elsevier Science Publishing Co., Inc. 1988) have further reviewed the role of the Vitamin K dependent proteins in coagulation.

Protein C has been shown to have major importance in vivo. Patients deficient in protein C, or its cofactor, protein S, show pronounced thrombotic tendencies. Babies born totally deficient in protein C exhibit massive disseminated intravascular coagulation (DIC) and a necrotic syndrome which leads to death within the first few weeks of life if untreated. Activated protein C has also been shown to protect animals against the coagulopathic and lethal effects of endotoxin shock, as described by Taylor, et al., in *J. Clin. Invest.* 79, 918–925 (1987).

As first reported by Kisiel, in *J. Clin. Invest.* 64, 761–769 (1979), Protein C was originally isolated in semi-pure form from plasma using classic protein purification techniques, including barium citrate adsorption and elution, ammonium sulfate fractionation, DEAE-Sephadex chromatography, dextran sulfate agarose chromatography, and preparative polyacrylamide gel electrophoresis. This procedure was vastly improved and facilitated by the discovery of a unique antibody to Protein C, designated HPC-4, described by Stearns, et al., in *J. Biol. Chem.* 263(2), 826–832 (1988). As detailed by Esmon, et al., at the Joint IABS/CSL Symposium on Standardization in Blood Fractionation including Coagulation Factors, Melbourne, Australia 1986 (reported in *Develop. Biol. Standard.*, 67, 51–57 (S. Karger, Basel, 1987), Protein C can be isolated from human plasma by batch adsorption of diluted heparinized plasma on QAE Sephadex, washing with buffered 0.15 M NaCl and eluting with 0.5 M NaCl, recalcifying and batch adsorbing with HPC-4, then washing with a $Ca^{2+}$ containing buffer and eluting the Protein C with an EDTA containing buffer. HPC-4 is a calcium-dependent monoclonal antibody to human protein C. The epitope recognized by the antibody has been identified and corresponds to the stretch of amino acids in the zymogen of protein C which spans the thrombin cleavage site. Activated protein C is not recognized by HPC-4. HPC-4 is disclosed and claimed in U.S. Pat. No. 5,202,253 to Esmon, et al.

Several antibodies to human protein C have been reported, for example, by Laurell, et al., *FEBS Letts.* 191(1), 75–81 (1985); Wakabayashi, et al., *J. Biol. Chem.* 261, 11097–11105 (1986); Sugo, et al., *Thromb. Hemost. Abstrs., Brussells,* 229 (1987); and Ohlin, et al., *J. Biol. Chem.* 262, 13798–13804 (1988). Some of these are calcium dependent, for example, one of the antibodies reported by Laurell, et al. However, as far as can be determined in the published reports, this dependence is due to the requirement for calcium binding to the light chain of protein C and the antibodies recognize epitopes on the light chain. Other antibodies recognize the region around the thrombin cleavage site on the heavy chain, but these are not calcium dependent. The HPC-4 antibody of Ohlin, et al., is $Ca^{2+}$ dependent but is not directed against the activation region, and is therefore different from the antibody described in Stearns, et al., and in U.S. Pat. No. 5,202,253 to Esmon, et al.

All of the other antibodies that bind to the $Ca^{2+}$ stabilized regions of Protein C recognize both Protein C and the activated form of Protein C. Situations may arise in which the protein uncontaminated by its active form is desirable. This is particularly the case with reference to therapeutic uses of the antibody to inhibit Protein C activation.

Blockage of the natural anticoagulant pathways, in particular the protein C pathway, uses the natural procoagulant properties of the tumor to target the tumor capillaries for microvascular thrombosis, leading to hemorrhagic necrosis of the tumor, as described in U.S. Pat. No. 5,147,638 to Esmon, et al. HPC-4 is a preferred antibody for use in this method for the treatment of solid tumors, either alone or in conjunction with biological response modifiers, chemotherapy or radiation treatments.

Tumors contain proteins which predispose to the formation of blood clots in the vessels in the tumor bed. Tumors also contain other proteins and cellular elements which prevent thrombosis of tumor blood vessels. Tumor necrosis results from altering the hemostatic balance between procoagulant and anticoagulant mechanisms to favor thrombosis of the tumor microvasculature. The hemostatic balance of the tumor can be altered by blocking the conversion of protein C to its active form (activated protein C). The procoagulant mechanisms present in the tumor bed will then function without opposition and cause thrombosis of the tumor vessels. The epitope for the HPC-4 antibody spans the activation site in protein C and as a result blocks protein C activation. As an experimental tool it is important to note that the antibody cross-reacts with protein C from canine, porcine and at least two primate plasmas, baboon and marmoset. It does not cross-react with bovine or mouse protein C. The inhibitory effect can be reversed instantly by administration of activated protein C to which the antibody does not bind. The antibody therefore provides a means to selectively inhibit the protein C pathway in vivo and to reverse the process if thrombotic complications ensue at sites other than the tumor. The Protein C blocking agent is preferably administered in combination with a cytokine that stimulates natural killer and lymphokine-activated killer cell-mediated cytotoxicity, activates macrophages, stimulates Fc receptor expression on mononuclear cells and antibody-dependent cellular cytotoxicity, enhances HLA class II antigen expression, and/or stimulates procoagulant activity, such as tumor necrosis factor (TNF), interleukin-1 (IL-1), interleukin-2 (IL-2), gamma interferon (gamma-IFN), or granulocyte-macrophage colony stimulating factor (GMCSF). Alternatively, an agent such as endotoxin, or the purified liposaccharide (LPS) from a gram negative bacteria such as E. coli, can be used to elicit production of cytokines such as TNF.

HPC-4, despite its wonderful properties, is a murine antibody. It would be advantageous to be able to provide a humanized form of the antibody which is non-immunogenic or less immunogenic. In order to construct a humanized form of HPC-4 it is essential to know the sequence of the hypervariable regions of this antibody. Then using conventional mutagenesis methods developed in molecular biology it is possible to replace the sequence of hypervariable regions of an unrelated human antibody with the sequences of HPC-4 hypervariable regions. Such an approach has been successfully used in the humanization of other antibodies. Furthermore by knowing the sequence of the hypervariable region it may be possible to synthesize short peptides corresponding to the hypervariable regions of the HPC-4 antibody which could mimic HPC-4 and bind to the same region on protein C and prevent activation of protein C by thrombin-thrombomodulin complex. Such peptides could be very effective in disease states where promoting of the clotting is desired.

It is therefore an object of the present invention to provide a recombinant $Ca^{2+}$ dependent antibody which binds to the activation region of Protein C like HPC-4.

It is a further object of the present invention to provide a DNA sequence encoding the hypervariable region of an antibody like HPC-4.

It is a still further object of the present invention to provide a method and means for using this $Ca^{2+}$ dependent antibody for therapeutic purposes.

It is yet another object of the present invention to provide this $Ca^{2+}$ dependent antibody, antibodies, peptide derivatives and conjugates thereof, for diagnostic purposes.

SUMMARY OF THE INVENTION

The amino acid and nucleic acid sequences of the hypervariable regions of the HPC-4 antibody have been determined and used in the construction of "humanized antibodies". Peptides derived from the hypervariable regions are also disclosed which are useful in mimicking HPC-4—protein C binding. These materials are useful in isolation of protein C, treatment of tumor patients, and as inhibitors of coagulation, as well as in diagnostic assays.

DETAILED DESCRIPTION OF THE INVENTION

The variable heavy (VH) and the variable light (VL) chains of a $Ca^{2+}$ dependent monoclonal antibody that specifically binds to a specific twelve peptide sequence E D Q V D P R L I D G K (Sequence ID No. 1), in the activation region of the Protein C of non-bovine origin, including human, pig, baboon, and canine Protein C, in combination with calcium, has been cloned and sequenced. The antibody does not bind to activated protein C ("APC") and can be used to inhibit activation of Protein C by thrombin-thrombomodulin. As described below, the Fab (fragment antigen binding) sequence of the HPC-4 antibody was constructed in a bacterial periplasmic expression vector and the recombinant antibody was isolated from bacterial cell culture supernatants in large quantities by affinity chromatography using the peptide sequence described above bound to an immobilized substrate.

The antibody has a number of specific uses in isolation and characterization of Protein C, as a diagnostic, and as a therapeutic to prevent activation of Protein C. In vivo, a humanized recombinant antibody has been demonstrated to inhibit tumor growth. Further, the antibody is effective in promoting clotting in patients having high levels of Factor VIII inhibitors, hemophilia, platelet deficiencies (thrombocytopenia), and other clotting disorders where it is desirable to increase clotting.

Antibody Structure and Specificity

X-ray crystallographic studies have provided structures of antibody molecules and have revealed the nature of antigen-antibody recognition. Antibodies are large proteins (approximately 150,000 daltons in the case of an immunoglobulin G), that consist of four polypeptide chains: two identical heavy chains and two identical light chains. The antigen-binding site consists of roughly the first 110 amino acids of the heavy and light chains, and is termed the variable region. Antibodies bind molecules with association constants that range from $10^4$ to $10^{14}$ $M^{-1}$. Small molecules, typically from 100 to 2500 Daltons, are typically bound in the cleft of the antibody molecule, but for large molecules, for example, from 10 KDa to 500 KDa, the binding site can be an extended surface that can cover 600 to 800 Å. The specificity of antibodies for their ligands can exceed that of enzymes for substrates.

Recombinant antibodies are constructed that typically consist of the hypervariable regions of the heavy and light chains of the antibody from which the sequence is derived, in this case HPC-4, which may be crosslinked or coupled to other antibody domains or fusion proteins as discussed in more detail below. The antibody can be modified by site directed mutagenesis of the coding sequence, commonly used in molecular biology to alter affinity or specificity, as well as humanized to improve in vivo utility.

HPC-4 Antibody

The properties of the monoclonal antibody, HPC-4, deposited with the American Type Culture Collection, Rockville, Md., on Nov. 2, 1988, and assigned ATCC No. HB 9892, which make it uniquely useful are as follows:

The antibody binds protein C, not activated protein C (APC), and only in the presence of calcium. Thus, when the antibody is immobilized on an affinity support, protein C can be isolated from either plasma-derived sources or from tissue culture expression systems under extremely mild conditions. This is important in maintaining the biological activity of the product and the stability of the solid support resin. Since activated protein C is not bound under any conditions, the resulting product is completely free of APC.

The antibody binds to the activation site on protein C and can therefore be used to block the formation of the anticoagulant protein APC in vivo. Since it does not bind to or inhibit APC, the in vivo inhibitory effects can be reversed by administration of APC.

Cloning and Sequencing of HPC-4 DNA

Methods

Construction of the HPC-4 cDNA Library: RNA from approximately $1\times10^8$ HPC-4 hybridoma cells grown in 75 ml T-flasks was prepared and mRNA (PolyA+RNA) was isolated on oligo(dT)-cellulose according to the manufacturer's instruction (Stratagene, Calif.). Approximately 10 μg of PolyA+RNA was used to synthesize first and then second-strand cDNA according to established procedures. Using standard molecular biology techniques, EcoRI linkers were ligated to double stranded cDNA (ds cDNA) and the ds cDNA ligated to phage lambda (lambda gt10) vector DNA which has been digested with EcoRI. The HPC-4 cDNA and lambda gt10 phage vector ligation mixture was packaged in vitro and transformed into C600hflA strain of *E. coli*, and plated onto agar plates at high density. The bacteriophage plaques were then transferred to Gene Screen Plus™ filters (New England Nuclear) and probed with $^{32}$P labeled cDNA fragments derived from constant regions of an unrelated immunoglobulin heavy chain (Tasuku Honjo et al, *Cell* 18:559–568, 1979) and light chain genes (Edward Max et al, *J. Biol. Chem.* 256:5116–5120, 1981).

Several positive clones from heavy chain and light chain plates were identified. Phage DNA were prepared and the inserts were cleaved by the EcoRI restriction enzyme. The clones identified by heavy chain or light chain probes gave an insert of approximately 1600 or 800 bp, respectively. The heavy and light chain cDNA fragments were subcloned into EcoRI site of pUC19 plasmid and sequenced by the universal pUC forward and reverse sequencing primers.

Cloning by PCR: The variable regions of heavy (VH) and light chain (VL) of HPC-4 monoclonal antibody were cloned by the PCR method as well. After first strand cDNA synthesis, poly(dG) tail was added to the 3' end of first strand with terminal deoxynucleotidyl transferase (TdT). For cloning of the VH region the product then was amplified with the antisense primer derived from the 3' end of the heavy chain constant region 5'-AAGCGGCCGCTGGATAGACA-GATGGGGGTGTCGTTTTGCC-3' (Sequence ID No. 2) and another oligonucleotide primer consisting of a poly(dC) tail AAGCGGCCGCCCCCCCCCCCCCCCCCCCC-3' (Sequence ID No. 3). Similarly, for cloning of the VL region the poly(dG) tailed first strand DNA was amplified with the antisense primer derived from the 3' end of the light chain constant region 5'-AAGCGGCCGCGAAGATGGATA-CAGTTGGTGCAGCATCAGC-3' (Sequence ID No. 4) and the other oligonucleotide containing the poly(dC) tail (Sequence ID No. 3). The PCR amplified products which were approximately 400 bp each were separately subcloned into the SmaI site of pUC19 plasmid and sequenced by the universal forward and reverse sequencing primers.

The sequences of the heavy and light chain variable region by both methods of cloning (PCR or lambda gt10 library) were found to be identical.

Expression of HPC-4 Fab in bacteria: The Fab (fragment antigen binding) sequence of HPC-4 was amplified from the heavy and light chain cDNA by the PCR methods for expression as outlined briefly below: The Fab region of an antibody is made of VH and the constant heavy chain domain 1 (CH1) held together with VL and the constant light chain (CL). To express HPC-4 Fab in bacteria, four PCR primers were synthesized: The heavy chain forward primer was 5'-AGGTTACTCTGCTCGAGTCTGGCCCTGG-3' (Sequence ID No. 5) which was designed to have a XhoI restriction enzyme site for construction purposes. The heavy chain reverse primer (complementary to the 3' end of CH1 region) 5'-AGGCCTACTAGTTTACTAACAATC-CCTGGGCACAAT-3' (Sequence ID No. 6) was synthesized with two stop codons and an SpeI site after the stop codons. Similarly, a light chain forward primer 5'-TGTCCAGAG-GAGAGCTCATTCTCACCCAGTCTCCGGC-3' (Sequence ID No. 7) was synthesized which contained a SacI restriction enzyme site and the reverse primer 5'-TCCT-TCTAGATTACTAACACTCTCCCCTGTTGAA-3' (Sequence ID No. 8) contained two stop codons and an XbaI site for construction purposes. The heavy and light chain HPC-4 cDNA were amplified by these primers and the resulting DNA fragments were subcloned into Immuno ZAP H™ and Immuno ZAP L™ vectors, respectively, according to the manufacturer's instruction (Stratagene, Calif.).

The HPC-4 Fab was expressed in the periplasmic space of bacteria (XL1-B strain of *E.Coli*) and purified on its own 12 residue epitope from human protein C activation peptide region (Glu-Asp-Gln-Val-Asp-Pro-Arg-Leu-Ila-Asp-Gly-Lys (Sequence ID No. 1), linked to Affigel™. The HPC-4 Fab was eluted with TBS (20 mM Tris HCl, pH 7.5, 0.1 M NaCl) containing 5 mM EDTA, indicating that the binding of Fab fragment of HPC-4 to its epitope, like the full length native HPC-4 antibody, is Ca$^{2+}$ dependent. SDS-PAGE of purified Fab indicated that the purified Fab is essentially pure and as expected it migrated with an apparent molecular mass of 48 KDa. All indications are that recombinant HPC-4 Fab contains all the properties of wild type HPC-4 monoclonal purified from ascites. It should be noted that the cloning strategies used in Immuno ZAP™ expression system changes the native threonine (amino acid at position 3) to Lysine and Lysine at position 5 to Leucine, in the heavy chain. In the light chain the native HPC-4 contains Glutamine and Isoleucine at the position 1 and 2 of the mature peptide and the cloning strategy changes them to Glutamic acid and Leucine, respectively. These minor changes at the N-terminus of the heavy and light chain which are outside the regions where the epitope binds during expression in bacteria do not effect the properties of HPC-4 Fab as evidenced by its similar Ca$^{2+}$—dependent affinity binding to the 12 amino acid residue peptide epitope determined by intrinsic fluorescence spectroscopy.

Using these techniques, the following nucleic acid and amino acid sequences were obtained:

1. Nucleotide sequence encoding HPC-4 Heavy chain variable region (VH Gamma) (Sequence ID No. 9):

```
ATGGGCAGGC TTTCTTCTTC ATTCTTGCTA CTGATTGCCC

CTGCATATGT CCTGTCCCAG GTTACTCTGA AAGAGTCTGG

CCCTGGGATA TTGCAGCCCT CCCAGACCCT CACTCTGACT

TGTTCTCTCT CTGGGTTTTC ACTGAGGACT TCTGGTATGG

GTGTAGGCTG GATTCGTCAG CCTTCAGGGA AGGGTCTGGA

GTGGCTGGCA CACATTTGGT GGGATGATGA CAAGCGCTAT

AACCCAGTCC TGAAGAGCCG ACTGATAATC TCCAAGGATA

CCTCCAGGAA ACAGGTATTC CTCAAGATCG CCAGTGTGGA

CACTGCAGAT ACTGCCACAT ACTACTGTGT TCGAATGATG

GATGATTACG ACGCTATGGA CTACTGGGGT CAAGGAACCT

CAGTCACCGT CTCCTCT.
```

The signal peptide is encoded by nucleotides 1 to 57. The mature peptide (form that is expressed) is encoded by nucleotides 58 to 417.

2. The HPC-4 heavy chain variable region amino acid sequence including the signal sequence (Sequence ID No. 10) is as follows:

MGRLSSSFLL LIAPAYVLSQ VTLKESGPGI LQPSQTLTLT CSLSGFSLRT SGMGVGWIRQ PSGK-

GLEWLA HIWWDDDKRY NPVLKSRLII SKDTSRKQVF LKIASVDTAD TATYYCVRMM DDYDAMDYWG QGTSVTVSS.

The mature peptide starts at amino acid No. 20 which is a Q. Standard one-letter abbreviations for amino acids are used.

3. Nucleotide sequence encoding HPC-4 light chain variable region (VL Kappa) (Sequence ID No. 11) is as follows:

```
ATGGATTTTC AGGTGCAGAT TTTCAGCTTC CTGCTAATCA

GTGCCTCAGT CATAATGTCC AGAGGACAAA TTATTCTCAC

CCAGTCTCCG GCAATCATGT CTGCATCTCT GGGGGAGGAG

ATCACCCTAA CCTGCAGTGC CACTTCGAGT GTAACTTACG

TCCACTGGTA CCAGCAGAAG TCAGGCACTT CTCCCAAACT

CTTGATTTAT GGGACATCCA ACCTGGCTTC TGGAGTCCCT

TCTCGTTTCA GTGGCAGTGG GTCTGGGACC TTTTATTCTC

TCACAGTCAG CAGTGTGGAG GCTGAAGATG CTGCCGATTA

TTACTGCCAT CAGTGCAATA GTTATCCGCA CACGTTCGGA

GGGGGGACCA AGCTGGAAAT AAAACGG.
```

The signal peptide is encoded by nucleotides 1 to 66. The mature peptide is encoded by nucleotides 67 to 387 (starts at CAAATTA . . . ).

4. The HPC-4 light chain variable region amino acid sequence (Kappa chain) (Sequence ID No. 12) is as follows.

```
MDFQVQIFSF LLISASVIMS RGQIILTQSP AIMSASLGEE

ITLTCSATSS VTYVHWYQQK SGTSPKLLIY GTSNLASGVP

SRFSGSGSGT FYSLTVSSVE AEDAADYYCH QWNSYPHTFG

GGTKLEIKR.
```

The mature peptide starts at amino acid 23 which is a Q.

Those skilled in the art will realize that a variety of DNA sequences would code for the polypeptide antibody fragments described above. This is due to existence of the degeneracy of the genetic code, which means that different codons (sets of three bases) can code for the same amino acid residue. These are known to those skilled in the art. It is also possible to synthesize DNA sequence having different additional substitution than those described above but which would still code for a protein having the same binding specifications, for example, which has conservative amino acid substitutions, i.e., substitutions of one amino acid with another of similar size and charge.

Construction of Recombinant Antibodies.

Using the sequences disclosed above, recombinant antibodies can be constructed using known methodology. Methods for constructing chimeric genes have been described by, for example, Kobilka, B. K., et al, "Chimeric $\alpha_2$-,$\beta_2$-Adrenergic Receptors: Delineation of Domains Involved in Effector Coupling and Ligand Binding Specificity" *Science* 240:1310–1316, 1988; Verhoeyen, M., C. Milstein, G. Winter, "Reshaping Human Antibodies: Grafting an Antilysozyme Activity," *Science*, 239:1534–1536, 1988; Riechmann, L., M. Clark, H Waldmann, G. Winter, "Reshaping human antibodies for therapy," *Nature*, 332: 323–327, 1988). Using standard molecular biology techniques, the target DNA, containing the gene for the monoclonal antibody of interest can be constructed into appropriate expression vectors, such as baculovirus expression vectors, according to the procedures described in Summers, M. D. and G. E. Smith, "A manual of methods for baculovirus vectors and insect cell culture procedures", Texas Agricultural Experimental Station (1987). Expression of the recombinant gene can be achieved by the methods described therein, the teachings of which are incorporated herein. Alternatively, recombinant antibodies can be produced in bacterial periplasmic expression vectors such as those described above. Screening for the desired product can be achieved by ELISA assay wherein released protein is tested for its ability to recognize the antigen for which the target immunoglobulin was specific in a metal dependent manner.

Humanization of Antibodies

Methods for "humanizing" antibodies, or generating less immunogenic fragments of non-human antibodies, are well known. A humanized antibody is one in which only the antigen-recognizing sites, or complementarity-determining hypervariable regions (CDRs) are of non-human origin, whereas all other regions including the framework regions (FRs) of variable domains are products of human genes. These "humanized" antibodies are less immunogenic when introduced into a human recipient yet they retain their antigen binding specificity. To accomplish humanization of a selected mouse monoclonal antibody, the CDR grafting method described by Daugherty, et al., *Nucl. Acids Res.*, 19:2471–2476 (1991), incorporated herein by reference, can be used. Briefly, animal CDRs are distinguished from animal framework regions (FRs) based on locations of the CDRs in known-sequences of animal variable genes, (Kabat, H. A., et al., Sequences of Proteins of Immunological Interest, 4th Ed. U.S. Dept. Health and Human Services, Bethesda, Md., 1987). Once the animal CDRs and FRs are identified, the animal CDRs are grafted onto the sequence of an unrelated human heavy and light chain variable region frameworks by the standard molecular biology techniques including the use of synthetic oligonucleotides and polymerase chain reaction (PCR) methods. Alternatively, the entire sequences of a known human variable heavy and light chain gene in which all the codons encoding for the CDRs are replaced with the desired CDRs of animal antibody, are synthesized in the laboratory by a DNA synthesizer (Applied Biosystems Division of Perkin-Elmer Cetus, Calif.). The resulting synthetic DNA sequences encoding for the human heavy and light chain variable regions with grafted CDRs from animal antibody are subcloned into expression vectors and recombinant fusion antibodies are prepared in baculovirus or periplasmic space of bacteria as described above. Recombinant antibodies can be produced in mammalian expression systems as well.

The immunogenic stimulus presented by the monoclonal antibodies so produced may be also decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, the variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of antigenic epitopes, and thereby presents a much weaker immunogenic stimulus when injected into humans.

Purification of HPC-4 Antibody

Both HPC-4 from ascites and the recombinant HPC-4 bind to a defined region of the protein C molecule that is contained within residues 6 and 17 of the heavy chain, specifically E D Q V D P R L I D G K (Sequence ID No. 1). This peptide can be immobilized directly on a solid support resin and can be used to isolate the antibody in high concentrations from ascites fluid or as recombinant form from cell culture supernatants. This approach allows the isolation of the antibody in extremely pure form in high yield, even from very dilute solutions.

The antibody can be removed from the solid support peptide either by the removal of calcium ions, if desired, or by 1.5 M guanidine, which does not affect the function of the purified monoclonal antibody. This may be significant, as guanidine is recognized as a viral deactivation agent by regulatory agencies. After elution or treatment with this agent, the antibody will not contain any live virus which may be present either in the ascites fluid derived from the mice used to produce the monoclonal antibody or culture supernatants, if tissue culture for production of recombinant antibody was used. Accordingly, virus will not be introduced into the protein C product from the antibody used to prepare it.

In a preferred embodiment, the peptide is coupled to Affi-Gel™ 15 to give a final concentration of approximately 1.0 mg/ml. Coupling of the epitope peptide is performed in 0.1 M NaCl, 0.1 M MOPS, pH 7.5, at 4° C. as described by the manufacturer (Bio-Rad, Richmond, Calif.). The Affi-Gel™ is washed with ice cold water immediately before use to remove the organic solvent. The epitope peptide is prepared at a concentration of between 1 and 2 mg/ml in 0.1 M NaCl, 0.1 M MOPS, pH 7.5, and mixed with sufficient Affi-Gel™ 15 to give a final ratio of peptide to gel of 1 mg/ml. The peptide and the gel are mixed overnight (between approximately 12 and 18 h) on a gentle rocker to couple the peptide to the gel. After the coupling reaction is completed, the resin is poured into a glass column, and washed with 0.1 M NaCl 0.01 M MOPS, pH 7.5. 100 ml of resin has a capacity of at least 1.5 grams of HPC-4.

Human protein C can be coupled to the Affi-Gel™ by the same method. Three to five mg protein C/ml of the buffer described above is mixed with sufficient Affi-Gel™ 15 to give a final ratio of human protein C to gel of 3–5 mg protein/ml of gel.

The desalted ammonium sulfate fraction from the ascites is loaded onto the epitope affinity column, and the column is washed with at least 4 column volumes of 0.4 M NaCl, 0.02 M Tris HCl, 1 mM $CaCl_2$, pH 7.5. The HPC-4 or recombinant antibody is then eluted from the column in one of the following ways: (1) 2 M NaCl, 0.02 M Tris HCl, 2 mM EDTA; (2) 2 M NaCl, 1.5 M guanidine HCl, 0.02 M Tris HCl, 2 mM EDTA. The advantage of the latter is that the protein elutes as a much sharper peak, with concentrations of greater than 25 mg/ml when 200 ml of ascites is applied to a 100 ml column of resin. The antibody retains greater than 95% of the capacity to bind to the epitope after elution under these conditions. Antibody is then either dialyzed or desalted into the appropriate buffer for further applications. No contaminants of the antibody are detectable by SDS gel electrophoresis. Additional antibody can be obtained by applying the breakthrough material back to the column if the column is overloaded above its capacity.

Applications of HPC-4 Antibody In Vitro

The recombinant antibody can be utilized in the same way as HPC-4 for purification and therapeutic purposes. As discussed below, "HPC-4" includes both the deposited murine monoclonal antibody and recombinant forms thereof.

Purification of Protein C

For purification of protein C by affinity chromatography, coupling of the antibody to an immobilized substrate such as Affi-Gel™ resin is performed in 0.1 M NaCl, 0.1 M MOPS, pH 7.5, at 4° C. as described by the manufacturer (Bio-Rad, Richmond, Calif.). The Affi-Gel™ is washed with ice cold water immediately before use to remove the organic solvent. HPC-4 is prepared at a concentration of 3–5 mg/ml in 0.1 M NaCl, 0.1 M MOPS, pH 7.5, and mixed with sufficient Affi-Gel™ 10 to give a final ratio of HPC-4 to gel of 5 mg/ml. Antibody and the gel are mixed overnight (12–18 h) on a gentle rocker to allow the coupling reaction. Usually greater than 90% of the antibody is bound. After the coupling reaction is completed, the resin is poured into a glass column, and washed with 0.1 M NaCl 0.01 M MOPS, pH 7.5. The resin is stable at 4° C. under these conditions for at least one year. 100 ml of resin has a capacity of at least 20 milligrams of protein C.

As described above, the peptide can be used in the isolation and purification of HPC-4 by affinity chromatography. In a similar manner, the peptide can be used to temporarily "protect" the binding site during the process in which the antibody is bound to the chromatography substrate, to insure that the maximum amount of bound antibody is available for binding to the protein to be isolated. The reactive groups of the peptide which are capable of reacting with the chromatography substrate (amino terminal, lysine side chain), which are not required for recognition by HPC-4, are first blocked by reaction of the peptide with acetic anhydride using standard methods known to those skilled in the art. After the HPC-4 is coupled to the resin, the peptide bound in the antigen binding site of the antibody is removed by washing the resin with 1.5 M Guanidine HCl, 2 mM EDTA, 0.02 M Tris HCl, pH 7.5.

The antibody and peptide can be bound to a variety of substrates, for use in purification and isolation of Protein C and the antibody, respectively, including agarose, acrylamide and other types of conventional chromatographic resins, filters, etc. These materials are known to those skilled in the art, as are the methods for attaching the protein to them. The selection of the material will depend in large part on the scale of the purification or the sample to be analyzed, as well as biocompatibility and government agency approval where the end-product is for pharmaceutical use.

Diagnostic Applications

Methods and means for labeling the antibody for use as a diagnostic are known to those skilled in the art, including labelling with a radioactive, fluorescent, luminescent, or enzymatic molecule. The antibodies are then used in diagnostic assays to measure the amount of Protein C rather than Activated Protein C or total Protein C, since the antibody does not bind Activated Protein C, unlike other antibodies to Protein C.

Isolation of Fusion Proteins with Antibody

A fusion protein readily isolated by affinity chromatography using HPC-4 antibody is prepared by insertion of a DNA sequence encoding the twelve amino acid HPC-4 epitope into a vector, followed by the gene encoding the protein to be isolated as described in U.S. Pat. No. 5,298,599 issued Mar. 29, 1994. In the preferred embodiment, a specific protease cleavage site is inserted into the vector between the epitope and protein coding sequence, so that the resulting fusion protein can be easily cleaved to yield the epitope peptide and the desired protein. In the most preferred embodiment, the fusion protein includes a protease cleavage site between the epitope and the protein to be isolated. Suitable sites include sequences cleaved by Factor Xa: Ile Glu Gly Arg (IEGR), enterokinase: Asp Asp Asp Asp Lys (DDDDK), and thrombin: Phe/Gly Pro Arg (F/GPR). Following purification with the HPC-4, the fusion protein is treated with the appropriate enzyme to cleave the binding peptide from the desired protein.

Therapeutic Uses of Recombinant HPC-4

The coagulant and anticoagulant systems in mammals provide a delicate check and balance system which maintains blood in its proper fluid state. Alteration of any single element in this system can have an enormous impact on the ability of the mammal to maintain hemostasis.

The protein C system is an anticoagulant, regulatory system which inhibits blood coagulation and stimulates fibrinolysis. This system is activated by thrombin, an enzyme which converts fibrinogen to fibrin in the coagulative process. Free or excess thrombin binds with thrombomodulin, a protein on endothelial cells. The thrombin-thrombomodulin complex abolishes the ability of thrombin to catalyze clot formation and converts thrombin into a potent protein C activator. Activated Protein C in turn acts in combination with Protein S and a membrane surface to inactivate factor Va and factor VIIIa by limited proteolysis. The inactivated factor Va loses the ability to interact effectively with the enzyme factor Xa or the substrate prothrombin.

Addition of an antibody to Protein C, an antibody to Protein S, or addition of C4b binding protein (C4bBP), which binds Protein S to thereby inactivate it as a cofactor, in an appropriate form, can be used to promote clotting in individuals where it is desirable to do so. Patients having factor VIII inhibitors are representative of this group of patients. By preventing the factor Va from being inactivated, coagulation proceeds even in the relative absence of factor VIII.

The effect of administering these inhibitors of the Protein C anticoagulation system can be reversed by administration of excess amounts of activated Protein C or Protein S, depending on the agent used to block the pathway. The appropriate amount is based on calculations relating to the relative molar amounts of the proteins present in the blood. The feasibility of this approach to produce a hypercoaguable state has been demonstrated by the administration of HPC-4 to baboons (Taylor, et al, *J. Clin. Invest.*, 79, 918–925 (1987). When HPC-4 was present, the animals developed a massive coagulation response, characterized by total fibrinogen consumption, as the result of the infusion of low levels of bacteria. They did not develop this response in the absence of the antibody. Virtually identical results are obtained when C4bBP levels are elevated to approximately 1 mg/ml plasma. While these responses are detrimental to the animals, they illustrate that either method will enhance the coagulation system. This is beneficial in situations where normal hemostasis is impaired.

This method can also be applied in the treatment of other clotting factor deficiency states, including thrombocytopenia, for example, as induced by heparin or radiation therapy, liver disease and hemorrhagic stroke, both acutely and to minimize re-bleeding after the acute incident.

HPC-4 can also be used to induce microvascular clotting in a solid tumor bed, as described in U.S. Pat. No. 5,147,638 issued Sep. 5, 1992. In animal tumor models, this has been found to greatly impede growth of the tumor. The combination of this antibody and/or the other agents indicated above which are capable of blocking the function of the protein C anticoagulant pathway with other treatments presently in use, such as tumor necrosis factor or radiation, can also be used for treatment of solid tumors.

Pharmaceutical Compositions

Pharmaceutically acceptable carriers for administration of the antibodies include sterile normal saline at physiological pH. In the preferred method of administration, the agent is injected into the subject, most preferably, intravenously. Preferred dosages are between about 30 and about 150 μg antibody/ml patient plasma, which is sufficient to block greater than 90% of the endogenous protein C.

The teachings of the references and patents cited above are specifically incorporated herein as representative of methods and reagents known to those skilled in the art.

Modifications and variations of the present invention will be obvious to those skilled in the art from the foregoing detailed description. Such modifications and variations are intended to come within the scope of the appended claims.

The invention claimed is:

1. A recombinant Ca$^{2+}$ dependent monoclonal antibody or antibody fragment including a heavy chain and a light chain, wherein the antibody or antibody fragment comprise the hypervariable regions of the monoclonal antibody produced by the hybridoma deposited with the American Type Culture Collection as ATCC No. HB 9892, where the recombinant monoclonal antibody or antibody fragment bind an epitope in the activation peptide region of the heavy chain of Protein C defined by EDQVDPRLIDGK (Sequence ID No. 1) and calcium ions, where the antibody and antibody fragment inhibit Protein C activation by thrombin-thrombomodulin, and wherein the antibody and antibody fragment are expressed in bacterial or insect cells.

2. The recombinant antibody of claim 1 comprising an amino acid sequence selected from the group consisting of: MGRLSSSFLL LIAPAYVLSQ VTLKESGPGI LQPSQTLTLT CSLSGFSLRT SGMGVGWIRQ PSGKGLEWLA HIWWDDDKRY NPVLKSRLII SKDTSRKQVF LKIASVDTAD TATYYCVRMM DDYDAMDYWG QGTSVTVSS (Sequence ID No. 10); MDFQVQIFSF LLISASVIMS RGQIILTQSP AIMSASLGEE ITLTCSATSS VTYVHWYQQK SGTSPKLLIY GTSNLASGVP SRFSGSGSGT FYSLTVSSVE AEDAADYYCH QWNSYPHTFG GGTKLEIKR (Sequence ID No. 12); amino acids 20–139 of Sequence ID No. 10 and amino acids 23–129 of Sequence ID No. 12.

3. The recombinant antibody of claim 1 having coupled thereto a peptide sequence.

4. The recombinant antibody of claim 1 having a detectable label directly bound to the antibody.

5. The recombinant antibody of claim 1 immobilized to a substrate which does not interfere with the binding of said antibody to Protein C in combination with calcium ions, wherein the immobilized antibody is suitable for purification of Protein C from a biological fluid.

6. A composition comprising the recombinant antibody of claim 1 in combination with a pharmaceutically acceptable carrier for administration to a patient.

7. A recombinant Ca$^{2+}$ dependent monoclonal antibody or antibody fragment including a heavy chain and a light chain, wherein the antibody or antibody fragment comprise the hypervariable regions of the monoclonal antibody produced by the hybridoma deposited with the American Type Culture Collection as ATCC No. HB 9892, where the recombinant monoclonal antibody or antibody fragment bind an epitope in the activation peptide region of the heavy chain of Protein C defined by EDQVDPRLIDGK (Sequence No. 1) and calcium ions, where the antibody and antibody fragment inhibit Protein C activation by thrombin-thrombomodulin, and wherein the antibody and antibody fragment are humanized.

8. The recombinant humanized antibody of claim 7 coupled thereto a peptide sequence.

9. The recombinant humanized antibody of claim 7 having a detectable label directly bound to the antibody.

10. The recombinant humanized antibody of claim 7 immobilized to a substrate which does not interfere with the binding of the antibody to Protein C in combination with calcium ions, wherein the immobilized antibody is suitable for purification of Protein C.

11. A composition comprising the recombinant humanized antibody of claim 7 in combination with a pharmaceutically acceptable carrier for administration to a patient.

12. A method of making a recombinant Ca$^{2+}$ dependent monoclonal antibody which binds an epitope in the activation peptide region of the heavy chain of Protein C defined by E D Q V D P R L I D G K (Sequence ID No. 1) and calcium ions, where the antibody inhibits Protein C activation by thrombin-thrombomodulin, by expressing nucleotide molecules encoding the hypervariable region of the heavy and light chains of the monoclonal antibody expressed by the hybridoma deposited with the American Type Culture Collection as ATCC No. HB 9892 in bacteria or insect cells.

13. The method of claim 12 wherein the recombinant antibody comprises an amino acid sequence selected from the group consisting of:
MGRLSSSFLL LIAPAYVLSQ VTLKESGPGI LQPSQTLTLT CSLSGFSLRT SGMGVGWIRQ PSGKGLEWLA HIWWDDDKRY NPVLKSRLII SKDTSRKQVF LKIASVDTAD TATYYCVRMM DDYDAMDYWG QGTSVTVSS (Sequence ID No. 10); MDFQVQIFSF LLISASVIMS RGQIILTQSP AIMSASLGEE ITLTCSATSS VTYVHWYQQK SGTSPKLLIY GTSNLASGVP SRFSGSGSGT FYS- LTVSSVE AEDAADYYCH QWNSYPHTFG GGT-
KLEIKR (Sequence ID No. 12); amino acids 20–139 of
Sequence ID No. 10 and amino acids 23–129 of
Sequence ID No. 12.

14. The method of claim 12 further comprising directly binding a detectable label to the recombinant antibody.

15. The method of claim 12 further comprising immobilizing the recombinant antibody to a substrate which does not interfere with the binding of said antibody to Protein C in combination with calcium ions, wherein the immobilized antibody is suitable for purification of Protein C from a biological fluid.

16. The method of claim 12 wherein the nucleotide sequence encoding the recombinant antibody is ligated to a sequence encoding a peptide and the ligated nucleotide sequence is expressed in an expression system.

17. A method of making a recombinant humanized $Ca^{2+}$ dependent monoclonal antibody which binds an epitope in the activation peptide region of the heavy chain of Protein C defined by EDQVDPRLIDGK (Sequence No. 1) and calcium ions, where the antibody inhibits Protein C activation by thrombin-thrombomodulin, by expressing nucleotide molecules encoding the hypervariable region of the heavy and light chains of the monoclonal antibody expressed by the hybridoma deposited with the American Type Culture Collection as ATCC No. HB 9892 in bacteria or insect cells.

18. The method of claim 17 further comprising directly binding a detectable label to the recombinant humanized antibody.

19. The method of claim 17 further comprising immobilizing the recombinant humanized antibody to a substrate which does not interfere with the binding of the antibody to Protein C in combination with calcium ions, wherein the immobilized antibody is suitable for purification of protein C from biological fluid.

20. The method of claim 17 wherein the nucleotide sequence encoding the recombinant humanized antibody is ligated to a sequence encoding a peptide and the ligated nucleotide sequence is expressed in an expression system.

* * * * *

UNITED STATES PATENT AND TRADEMARK OFFICE
CERTIFICATE OF CORRECTION

PATENT NO. : 7,247,453 B1 Page 1 of 1
APPLICATION NO. : 08/259321
DATED : July 24, 2007
INVENTOR(S) : Alireza Rezaie et al.

It is certified that error appears in the above-identified patent and that said Letters Patent is hereby corrected as shown below:

In claim 2, column 21, line 51, delete "10and" and insert --10 and-- therefor.

Signed and Sealed this

Thirtieth Day of October, 2007

JON W. DUDAS
*Director of the United States Patent and Trademark Office*